United States Patent [19]
Descamps et al.

[11] Patent Number: 4,565,828
[45] Date of Patent: Jan. 21, 1986

[54] BENZOFURAN DERIVATIVES AND THEIR THERAPEUTIC USE

[75] Inventors: Marcel Descamps, Rosieres; Peter Polster, Beauvechain, both of Belgium

[73] Assignee: Sanofi, Paris, France

[21] Appl. No.: 628,208

[22] Filed: Jul. 5, 1984

[30] Foreign Application Priority Data

Jul. 18, 1983 [FR] France ................................. 83 11805

[51] Int. Cl.[4] ...................... A61K 31/34; C07D 307/80
[52] U.S. Cl. ...................................... 514/469; 549/468
[58] Field of Search ......................... 549/468; 514/469

[56] References Cited

U.S. PATENT DOCUMENTS 3,248,401 4/1966 Tondeur et al. ..................... 549/468
3,920,707 11/1975 Descamps et al. .................. 549/468

FOREIGN PATENT DOCUMENTS 1299247 12/1972 United Kingdom .

OTHER PUBLICATIONS

Hellenic Biochemical and Biophysical Society, Biochemistry & Biophysics Newsletter, Jun. 1981, No. 16.

Primary Examiner—Henry R. Jiles
Assistant Examiner—Bernard I. Dentz
Attorney, Agent, or Firm—Bacon & Thomas

[57] ABSTRACT

Benzofuran derivatives represented by the general formula:

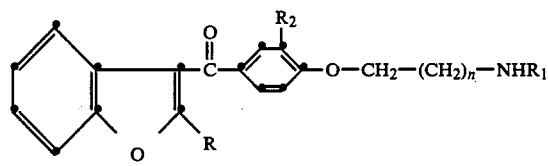

in which:
  R represents an ethyl, n-propyl, isopropyl or n-butyl radical;
  $R_1$ represents a branched-chain alkyl radical having from 4 to 7 carbon atoms of which at least one does not bear a hydrogen atom;
  $R_2$ represents hydrogen, chlorine or bromine;
  n is 1 or 2 and pharmaceutically acceptable acid addition salts thereof.

These derivatives have been found to possess calcium translocation inhibiting properties and antiadrenergic properties and can thus be used in the treatment of certain pathological syndromes of the cardiovascular system.

23 Claims, No Drawings

BENZOFURAN DERIVATIVES AND THEIR THERAPEUTIC USE

This invention relates to heterocyclic compounds and more particularly to novel benzofuran derivatives and the process used for their preparation. The benzofuran derivatives of this invention can be represented by the general formula:

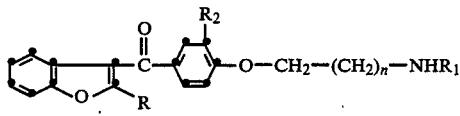

in which:

R represents an ethyl, n-propyl, isopropyl or n-butyl radical;

$R_1$ represents a branched-chain alkyl radical having from 4 to 7 carbon atoms of which at least one does not bear a hydrogen atom;

$R_2$ represents hydrogen, chlorine or bromine;

n is 1 or 2.

The invention also relates to the pharmaceutically acceptable acid addition salts of the compounds of formula I, for instance the hydrochloride. The benzofuran derivatives of the invention have been found to possess remarkable pharmacological properties, in particular those of a calcium translocation inhibitor as well as antiadrenergic properties. These properties are capable of rendering the compounds in question very useful in the treatment of certain pathological syndromes of the cardiovascular system, particularly in the treatment of angina pectoris, hypertension, arrhythmia and cerebral circulatory insufficiency.

In the antitumour field, the compounds of the invention can be a useful means of potentiating anticancer agents.

Consequently, the invention also relates to pharmaceutical and veterinary compositions containing, as the essential active ingredient, at least one benzofuran derivative of formula I, or a pharmaceutically acceptable addition salt thereof, in association with a pharmaceutical carrier or a suitable excipient.

A further object of the invention relates to a method of treating pathological syndromes of the cardiovascular system comprising the administration of an effective dose of at least one benzofuran derivative of the invention.

Depending on the administration route selected, the daily dosage for a human being weighing 60 kg will be from 2 to 500 mg of the essential active ingredient.

In accordance with the invention, the compounds of formula I can be prepared by condensing in an inert medium such as benzene, toluene, ethanol or a mixture of these solvents, a benzofuran compound of the general formula:

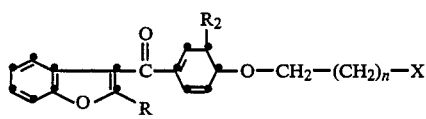

in which R and $R_2$ have the same meaning as above and X represents a halogen atom, preferably a bromine atom, or the p-toluenesulphonyloxy group, with an amine of the general formula:

$$H_2N-R_1 \qquad III$$

in which $R_1$ has the same meaning as in formula I, to form the required benzofuran derivative of formula I which, if desired, is reacted with the appropriate organic or inorganic acid to produce the pharmaceutically acceptable addition salt.

The condensation reaction in question is carried out at room-temperature or at a temperature between room-temperature and 80° C.

The compounds of formula II can be obtained:

(a) When X is a halogen, by condensing a benzofuran derivative of the formula:

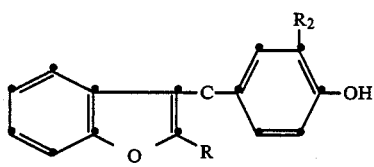

in which R and $R_2$ have the same meaning as in formula I, with a dihalogenated alkane of the general formula:

$$Hal-CH_2-(CH_2)_n-Hal \qquad V$$

in which Hal represents a halogen atom, preferably a bromine atom, and n has the same meaning as in formula I, in a solvent such as methyl ethyl ketone or dimethyl formamide and in the presence of an alkali metal carbonate, for instance potassium carbonate.

(b) When X is the p-toluenesulphonyloxy group, by condensing p-toluenesulphonyl chloride in pyridine with a benzofuran derivative of the general formula:

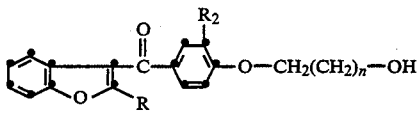

in which R, $R_2$ and n have the same meaning as in formula I.

Compounds of formula VI can be prepared by condensing, in a solvent such as dimethyl formamide and in the presence of an alkali metal carbonate, for instance potassium carbonate, a benzofuran derivative of formula IV with a halogenated alcohol of the general formula:

$$Hal-CH_2-(CH_2)_n-OH \qquad VII$$

in which Hal and n have the same meanings as in formula V.

In accordance with another method, compounds of formula II in which X represents a halogen are prepared, by the Friedel-Crafts reaction, by condensing, an acyl chloride of the formula:

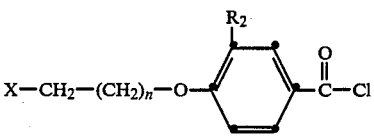

in which $R_2$ and n have the same meanings as in formula I and X represents a halogen atom, preferably a bromine atom, with a benzofuran derivative of the general formula:

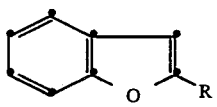

in which R has the same meaning as in formula I.

The compounds of formula IX are all known from French Pat. No. 1,260,578, whilst those of formula IV are also known compounds or compounds capable of being prepared in accordance with the methods in this French Patent.

Benzofuran derivatives substituted by a monoalkylaminoalkyloxybenzoyl chain and presented as having a pharmacological activity capable of rendering them useful in the treatment of angina pectoris are already known.

In this connection, mention may be made of French Pat. No. 2,242,087 which specifically describes the 2-n-butyl-3-[4-(3-methylamino- or 3-ethylamino- or 3-n-butylamino-propoxy-benzoyl]-benzofurans in the form of the hydrochloride. However, the patent in question contains no pharmacological test-results relating to the monoalkyl derivatives.

Furthermore, 2-n-butyl-3-[4-(2-ethylamino-ethoxy)-3,5-diiodo-benzoyl]-benzofuran is mentioned in the Hellenic Biochemical and Biophysical Society's Newsletter, June 1981, No. 16, pages 6–8, but there is no allusion to any pharmacological activity.

In addition, tests carried out within the framework of the present invention have shown that these known compounds are either devoid of antiadrenergic properties or possess them to such a slight degree that they are without any therapeutic significance.

In the context of this invention, it was unexpectedly discovered that, by replacing the straight-chain monoalkyl radical of the monoalkylaminoalkoxybenzoyl chain in the known compounds by a branched-chain monoalkyl radical in which at least one of the carbon atoms does not bear a hydrogen atom, for instance a tert-butyl or neopentyl radical, compounds are obtained which possess much stronger $\alpha$- and $\beta$-antiadrenergic properties than those shown by compounds of the prior art.

Furthermore, it was found that the calcium-antagonistic activities of the compounds of the invention are at least equal to if not greater than those observed in the tests carried out with the known compounds.

In contrast to the known compounds, it has thus been possible to establish, for the compounds of the invention, a pharmacological profile showing that the balance between the respective degrees of activity of the calcium-antagonistic factor and the $\alpha$- and $\beta$-antiadrenergic component of these compounds is such as to render them suitable for the treatment of, for example, angina pectoris.

In addition, the compounds of the invention are devoid of iodine atoms, unlike the ethylamino-benzofuran derivative mentioned in the Hellenic Biochemical and Biophysical Society's Newsletter referred to above and the compound amiodarone or 2-n-butyl-3-[4-(2-diethylamino-ethoxy)-3,5-diiodobenzoyl]-benzofuran, a product well known for its antianginous and antiarrhythmic properties.

Other non-iodinated active compounds are certainly required, since regular administration of substances containing iodine can lead to undesirable side-effects, particularly in regard to the thyroid gland. In addition, such substances can render any accurate examination of the thyroid extremely difficult. Finally, owing to their low degree of toxicity the compounds of the invention, may be used as medicines.

As reported in detail by R. CHARLIER in "Bruxelles Medical", No. 9, September 1969, pages 543–560, it is accepted that an antianginous medicament must possess the ability to antagonize cardiovascular reactions of the adrenergic type.

To this end, agents capable of blocking the $\alpha$-receptors have been put forward. However, the clinical application of such compounds to the treatment of angina pectoris remained unsuccesful, most probably because antagonists of the $\alpha$-receptors only induce very partial neutralization of the adrenergic system, the activity of the $\beta$-receptors being unaffected.

It is a fact that the most undesirable haemodynamic manifestations occurring during the painful episodes of angina pectoris are mainly of a cardiac nature and are therefore related to the $\beta$-receptors.

Concurrently, antagonistic medication of the $\beta$-adrenergic receptors has been suggested. This type of compound, of which the clinical significance is undeniable, diminishes the attacks of angina pectoris by reducing the work of the heart through a slowing-down of cardiac frequency. However, there is no decrease in peripheral arterial pressure which, on the contrary, rises as a result of the liberation of the $\alpha$-tonus.

Such medicaments, however, modify certain haemodynamic parameters in a way which, from the fundamental standpoint, constitutes a counter-effect unfavourable to angina pectoris subjects in particular and cardiac subjects in general. If the antiadrenergic aspect of the $\beta$-blockers is considered, it becomes obvious that only tachycardia and an increase in the force and rapidity of the cardiac contraction are susceptible of being neutralized, since arterial hypertension depends on stimulation of the $\alpha$-receptors on which $\beta$-antagonists have no effect.

Although the cardiovascular disturbances caused by stimulation of the $\beta$-receptors are the factors most unfavourable to anginous patients, the fact remains that arterial hypertension also plays a not inconsiderable role. In addition, blocking of the $\beta$-receptors entails the risk of depriving the cardiac-insufficiency subject of a compensatory mechanism which he normally sets in motion to limit his circulatory insufficiency.

This reflex mechanism, the main component of which follows the course of the $\beta$-adrenergic system, results in particular in an increase in the force and rapidity of the cardiac contraction. Consequently, if this system is blocked, the functional disability of the cardiac-insufficiency subject deteriorates. Hence, it is logical to consider that the use of a $\beta$-blocker of which the action is pure and complete will always entail a cardiac risk.

Consequently, it seems preferable not to seek complete $\alpha$- or $\beta$-antagonistic properties in view of the side-effects which they can cause in clinical practice. It would appear more logical to aim at reducing rather than suppressing the cardiovascular disturbances which characterize hyperstimulation of the adrenergic system as a whole.

The compounds of the invention attain this objective because their $\alpha$- and $\beta$-antiadrenergic properties are incomplete. Consequently, they can be regarded not as β-blockers but as adrenal moderators i.e., partial antagonists of the α- and β-adrenergic reactions that are potentially devoid of the above-described disadvantages of the β-blockers.

In addition, the calcium-antagonistic component determined in the compounds of the invention will enhance their cardiovascular pharmacological spectrum to a remarkable degree.

It is a fact that calcium ions acting at the level of the cells regulate the degree of vasoconstriction and, thereby, play a critical role in the anginal attack.

Calcium-antagonistic compounds act on the cellular membrane by selectively blocking calcium access to the contractile process in the arterial cell. It appears increasingly evident, at the present time, that the clinical results attained by the combination of calcium-antagonists and β-adrenergic antagonists are better than when each antagonist is administered separately (J.A.M.A. 1982, 247, pages 1911–1917).

In addition, it seems that there is, at the present time, no known β-blocker which also has an appreciable antagonistic action relative to calcium translocation.

From this point of view, the fact that the compounds of the invention have both a calcium-antagonistic component and an α- and β-antiadrenergic component will be of prime importance since they are susceptible of more extensive therapeutic applications than a β-blocker alone or a calcium-antagonist alone. As an example, mention may be made of 2-n-butyl-3-[4-(2-neopentylamino-ethoxy)benzoyl]-benzofuran which has an α- and β-antiadrenergic component coupled with an oxygen-saving action capable of providing a therapeutic effect to human subjects in the effort angina syndrome which can, moreover, be treated by conventional β-blockers. However, the principal advantage of this compound lies in the fact that, because of its calcium-antagonistic component, it can be used in the treatment of angina at rest, a syndrome caused by the appearance of a spasm at the level of the coronaries which, at present, is combatted by compounds such as diltiazem, verapamil and nifedipine. The results of the pharmacological tests carried out to determine the cardiovascular properties of the compounds of the invention are set out below.

I. Calcium-antagonistic properties

The calcium translocation inhibition properties of the compounds of the invention with respect to cellular membrane have been determined by measuring their antagonistic action in regard to the contractile response to the depolarization induced by potassium on the isolated aorta of the rat.

It is a well established fact that the depolarization of the membrane of a smooth muscle by potassium renders the membrane permeable to extracellular calcium and causes muscular contraction.

Consequently, measurement of the inhibition of the contractile response to the depolarization produced by potassium or measurement of the relaxation of the tonic contraction provoked by potassium-induced depolarization can constitute a means of evaluating the power of a compound to inhibit the permeability of cellular membranes to $Ca^{++}$ ions.

The following technique was used:

The aorta was removed from male Wistar rats weighing about 300 g and cut into strips about 40 mm long and 3 mm wide. These pieces were placed in a 25 ml isolated-organ vessel containing modified Krebs bicarbonate solution (112 mM NaCl, 5 mM KCl, 25 mM $NaHCO_3$, 1 mM $KH_2PO_4$, 1.2 mM $MgSO_4$, 2.5 mM $CaCl_2$, 11.5 mM glucose, distilled water to 1000 ml), swept by a stream of carbon dioxide and kept at 37° C. The preparation was coupled to a force transducer and the contractile response was registered on a recorder after amplification.

A tension of 2 g was applied to the organ which was kept for 60 minutes in the modified Krebs bicarbonate solution and contractions were then induced by replacing the Krebs bicarbonate solution by Krebs potassium solution (17 mM NaCl, 100 mM KCl, 25 mM $NaHCO_3$, 1 mM $KH_2PO_4$, 1.2 mM $MgSO_4$, 2.5 mM $CaCl_2$, 11.5 mM glucose, distilled water to 1000 ml). As soon as the contractile response of the organ became reproducible, $10^{-6}$ mole of a compound of the invention was added to the bath. Sixty minutes later, a new spasm was induced by potassium depolarization.

The results obtained with the experimental aorta strips were expressed as percentages of the maximum contracting effect observed before treatment with the compound being tested.

Examples of the results obtained, the compounds of formula I being in the form of their hydrochlorides, are given hereunder:

| R | $R_1$ | $R_2$ | n | Percentage of maximum contracting effect |
|---|---|---|---|---|
| $C_2H_5$ | $CH_2-C-(CH_3)_3$ | H | 1 | 29.1 |
| $C_2H_5$ | $C-(CH_3)_3$ | H | 2 | 24.5 |
| $C_2H_5$ | $CH_2-C-(CH_3)_3$ | H | 2 | 25.7 |
| $n-C_3H_7$ | $C-(CH_3)_3$ | H | 1 | 43.3 |
| $n-C_3H_7$ | $CH_2-C-(CH_3)_3$ | H | 1 | 40.6 |
| $n-C_3H_7$ | $C-(CH_3)_3$ | H | 2 | 28.5 |
| $n-C_3H_7$ | $CH_2-C-(CH_3)_3$ | H | 2 | 19.8 |
| $iso-C_3H_7$ | $C-(CH_3)_3$ | H | 1 | 34.0 |
| $iso-C_3H_7$ | $C-(CH_3)_3$ | H | 2 | 7.3 |
| $iso-C_3H_7$ | $CH_2-C-(CH_3)_3$ | H | 2 | 21.4 |
| $iso-C_3H_7$ | $C-(CH_3)_3$ | Cl | 2 | 19.1 |
| $iso-C_3H_7$ | $CH_2-C-(CH_3)_3$ | Cl | 2 | 24.5 |
| $n-C_4H_9$ | $C-(CH_3)_3$ | H | 1 | 34.8 |
| $n-C_4H_9$ | $CH_2-C-(CH_3)_3$ | H | 1 | 29.4 |
| $n-C_4H_9$ | $C-(CH_3)_3$ | H | 2 | 34.0 |
| $n-C_4H_9$ | $CH_2-C-(CH_3)_3$ | H | 2 | 31.3 |

For purposes of comparison, the results set out below were obtained with the known compounds indicated:

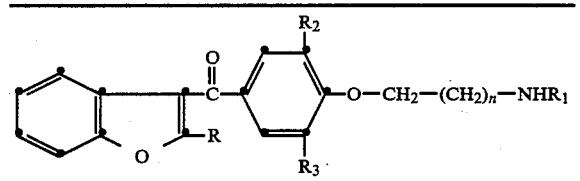

| R | $R_1$ | $R_2$ | $R_3$ | n | Percentage of maximum contracting effect |
|---|---|---|---|---|---|
| $n-C_4H_9$ | $C_2H_5$ | H | H | 2 | 80.6 |
| $n-C_4H_9$ | $n-C_3H_7$ | H | H | 2 | 73.4 |
| $n-C_4H_9$ | $n-C_4H_9$ | H | H | 2 | 58.5 |
| $n-C_4H_9$ | $C_2H_5$ | I | I | 1 | 85.1 |

These results show that the majority of the compounds of the invention are more active than the compounds known to be calcium-antagonists.

II. Antiadrenergic properties

The purpose of this test was to determine the capacity of the compounds of the invention to reduce the rise in blood-pressure provoked by epinephrine (anti-α effect) and the acceleration of cardiac frequency induced by epinephrine (anti-β effect) in the dog previously anaesthetized with pentobarbital and atropinized.

Anti-α effect

The first step taken was to determine for each dog the dose of epinephrine required (5–10 μg/kg) to give a reproducible rise of about 100 mmHg in arterial pressure.

The dose of epinephrine determined in this way was then administered, followed by the intravenous administration of 10 mg/kg of the compound to be studied. The reduction of hypertension obtained with the compound under study was then recorded as a percentage of the hypertension previously induced (about 100 mmHg).

Anti-β effect

During the same test as the one just described, the epinephrine caused a reproducible increase in heart-rate of about 70 beats/min. The reduction in the acceleration of the heart-rate obtained with the compound under study was then recorded as a percentage of the tachycardia previously induced (about 70 beats). In both cases, the degrees of reduction obtained were expressed as follows:

(+) for virtually no reduction
+ for a reduction <50%
++ for a reduction ≧50%
+++ for a subtotal reduction (almost complete reduction).

The results recorded are as follows

| R | $R_1$ | $R_2$ | n | Anti-α effect | Anti-β effect |
|---|---|---|---|---|---|
| $C_2H_5$ | $C-(CH_3)_3$ | H | 2 | ++ | ++ |
| $C_2H_5$ | $CH_2-C-(CH_3)_3$ | H | 2 | ++ | ++ |
| $n-C_3H_7$ | $CH_2-C-(CH_3)_3$ | H | 1 | ++ | ++ |
| $n-C_3H_7$ | $C-(CH_3)_3$ | H | 2 | ++ | ++ |
| $n-C_3H_7$ | $CH_2-C-(CH_3)_3$ | H | 2 | ++ | ++ |
| $iso-C_3H_7$ | $C-(CH_3)_3$ | Cl | 2 | +++ | +++ |
| $iso-C_3H_7$ | $CH_2-C-(CH_3)_3$ | H | 2 | ++ | ++ |
| $n-C_4H_9$ | $CH_2-C-(CH_3)_3$ | H | 1 | +++ | +++ |
| $n-C_4H_9$ | $C-(CH_3)_3$ | H | 2 | +++ | +++ |
| $n-C_4H_9$ | $CH_2-C-(CH_3)_3$ | H | 2 | +++ | +++ |

For purposes of comparison, similar tests were carried out with the following known compounds and the results indicated were obtained:

| R | $R_1$ | $R_2$ | $R_3$ | n | Anti-α effect | Anti-β effect |
|---|---|---|---|---|---|---|
| $n-C_4H_9$ | $C_2H_5$ | H | H | 2 | (+) | (+) |
| $n-C_4H_9$ | $n-C_3H_7$ | H | H | 2 | + | + |
| $n-C_4H_9$ | $n-C_4H_9$ | H | H | 2 | (+) | + |
| $n-C_4H_9$ | $C_2H_5$ | I | I | 1 | (+) | (+) |

These results prove that the α- and β-antiadrenergic activities of the compounds of the invention are much greater than those of the compounds of the prior art. Pharmaceutical compositions according to the invention may be presented in any form suitable for administration in human or veterinary medicine.

A dosage unit may take the form of, for example, a coated or uncoated tablet, a hard- or soft-gelatin capsule, a packaged powder or a suspension or syrup for oral administration, a suppository for rectal administration or a solution or suspension for parenteral administration.

A dosage unit may contain, for example, 50 to 500 mg of active ingredient for oral administration, 50 to 200 mg of active ingredient for rectal administration or 50 to 150 mg of active ingredient for parenteral administration. Depending on the administration route selected, the pharmaceutical or veterinary compositions of the invention will be prepared by associating at least one of the compounds of formula I, or a pharmaceutically acceptable acid addition salt thereof, with an appropriate excipient which may consist, for example, of one or more ingredients selected from the following substances: lactose, starches, talc, magnesium stearate, polyvinylpyrrolidone, alginic acid, colloidal silica, distilled water, benzyl alcohol or flavouring agents.

The following non-limitative Examples serve to illustrate the invention:

EXAMPLE 1

2-n-Butyl-3-[4-(2-tert-butylamino-ethoxy)-benzoyl]-benzofuran hydrochloride (a)

2-n-Butyl-3-[4-(2-bromo-ethoxy)-benzoyl]-benzofuran

A mixture of 93.5 g (0.25 mole) of 2-n-Butyl-3-(4-hydroxy-benzoyl)-benzofuran, 69 g (0.5 mole) of finely ground anhydrous potassium carbonate and 500 ml of methyl ethyl ketone was stirred and refluxed for 30 minutes. The mixture was allowed to cool to about 50° C. and 187.8 g (1 mole) of 1,2-dibromo-ethane were added in one operation. Stirring and refluxing were continued for 18 h and a further increment of 47 g of 1,2-dibromo-ethane was added. Refluxing was continued for 6 h, the course of the reaction being monitored by thin-layer chromatography (TLC). Filtration and evaporation to dryness under reduced pressure then followed. The residue was taken up in diethyl ether after which the ethereal solution was washed, first with water, then with a 10% aqueous solution of sodium hydroxide and once again with water. Drying was carried out over sodium sulphate, followed by evaporation to dryness under reduced pressure. In this way 56.5 g of 2-n-butyl-3-[4-(2-bromo-ethoxy)-benzoyl]-benzofuran in the form of an oil were obtained.

Yield: 60%

M.P.: 46°–47° C. (isopropanol)

By using the procedure described above but starting with the appropriate reactants and, as necessary, carrying out chromatographic purification on a silica column and, where required, crystallization in an appropriate solvent, the following compounds were obtained:

2-Isopropyl-3-[4-(2-bromo-ethoxy)-benzoyl]-benzofuran

Yield: 37%

Chromatography. M.P.: 102°–103° C. (petroleum ether, 80°–100° C.)

2-Isopropyl-3-[4-(3-bromo-propoxy)-benzoyl]-benzofuran

Yield: 49%

Chromatography. Oily product.

Similarly, the compounds mentioned below were prepared by the same procedure but in this case in dimethylformamide at room-temperature or, if necessary, at the higher temperature of 50°–90° C.

2-Ethyl-3-[4-(3-bromo-propoxy)-benzoyl]-benzofuran

Yield: 80%

Chromatography. Viscous oil.

2-n-Propyl-3-[4-(2-bromo-ethoxy)-benzoyl]-benzofuran

Yield: 50%

Chromatography. M.P.: 68°–70° C. (n-hexane).

2-n-Propyl-3-[4-(3-bromo-propoxy)-benzoyl]-benzofuran

Yield: 49%

Chromatography. Oily product.

2-Isopropyl-3-[3-chloro-4-(3-bromo-propoxy)-benzoyl]-benzofuran

Yield: 69%

Chromatography. Oily product.

2-n-Butyl-3-[4-(3-bromo-propoxy)-benzoyl]-benzofuran

Yield: 80%

Chromatography. Oily product.

2-n-Butyl-3-[3-bromo-4-(2-bromo-ethoxy)-benzoyl]-benzofuran

Yield (crude): 95%

Oily product.

2-n-Butyl-3-[3-chloro-4-(2-bromo-ethoxy)-benzoyl]-benzofuran

Yield (crude): 94%

Oily product.

2-n-Butyl-3-[3-chloro-4-(3-bromo-propoxy)-benzoyl]-benzofuran

Yield (crude): 89%

Oily product.

(b)

2-n-Butyl-3-[4-(2-tert-butylamino-ethoxy)-benzoyl]-benzofuran hydrochloride

A mixture of 13.2 g (0.0354 mole) of 2-n-butyl-3-[4-(2-bromo-ethoxy)-benzoyl]-benzofuran dissolved in 100 ml of benzene and 26 g (0.355 mole) of tert-butylamine dissolved in 60 ml of benzene was allowed to stand for 20 to 24 hours at a temperature of 50°–80° C., the course of the reaction being monitored by TLC. Evaporation to dryness was then carried out under vacuum and the residue taken up in diethyl ether and water to which a few ml of a 10% aqueous solution of sodium hydroxide had been added.

Extraction was then carried out with ether and the extracts suitably washed with water and subsequently dried over anhydrous sodium sulphate. Evaporation to dryness was carried out under vacuum and the residue was taken up in anhydrous ether and then acidified with an ethereal solution of hydrochloric acid.

The hydrochloride formed in this way was subsequently crystallized in methyl ethyl ketone and recrystallized in isopropanol.

In this way, 5.3 g of 2-n-butyl-3-[4-(2-tert-butylamino-ethoxy)-benzoyl]-benzofuran hydrochloride were obtained.

Yield: 35%

M.P.: 160°–162° C.

By following the foregoing procedure, but starting with the appropriate reactants and heating the reaction mixture to 50°–80° C., in a closed vessel, if necessary, the following compounds were prepared:

2-n-Propyl-3-[4-(2-tert-butylamino-ethoxy)-benzoyl]-benzofuran hydrochloride

Yield: 73%

M.P.: 164°–166° C. (ethyl acetate/methanol).

2-n-Propyl-3-[4-(3-neopentylamino-propoxy)-benzoyl]-benzofuran hydrochloride

Yield: 26%

M.P.: 139°–140° C. (methyl ethyl ketone).

2-Isopropyl-3-[4-(2-tert-butylamino-ethoxy)-benzoyl]-benzofuran hydrochloride

Yield: 88%

M.P.: 198°–201° C. (isopropanol)

2-Isopropyl-3-[4-(3-tert-butylamino-propoxy)-benzoyl]-benzofuran hydrochloride

Yield: 41%

M.P.: 159°–162° C. (cyclohexane/ethyl acetate).

By following the same procedure as that described above, but with the appropriate reactants and operating in an ethanol medium at a temperature of 50° to 60° C. for 16 to 20 hours, if necessary in a closed vessel, the following compounds were prepared:

2-Ethyl-3-[4-(3-tert-butylamino-propoxy)-benzoyl]-benzofuran hydrochloride

Yield: 53%

M.P.: 139°–142° C. (ethyl acetate)

2-Ethyl-3-[4-(3-neopentylamino-propoxy)-benzoyl]-benzofuran hydrochloride

Yield: 10%

M.P.: 125°–128° C. (ethyl acetate)

2-n-Propyl-3-[4-(2-neopentylamino-ethoxy)-benzoyl]-benzofuran hydrochloride

Yield: 87%

M.P.: 150°–151° C. (ethyl acetate)

2-Isopropyl-3-[4-(2-neopentylamino-ethoxy)-benzoyl]-benzofuran hydrochloride

Yield: 51%

M.P.: 146°–149° C. (methyl ethyl ketone)

2-Isopropyl-3-[4-(3-neopentylamino-propoxy)-benzoyl]-benzofuran hydrochloride

Yield: 56%

M.P.: 153°–156° C. (isopropanol)

2-Isopropyl-3-[3-chloro-4-(3-tert-butylamino-propoxy)-benzoyl]-benzofuran hydrochloride Yield: 84%

M.P.: 148°–150° C. (ethyl acetate)

2-Isopropyl-3-[3-chloro-4-(3-neopentylamino-propoxy)-benzoyl]-benzofuran hydrochloride Yield: 44%

M.P.: 138°–141° C. (ethyl acetate)

2-n-Butyl-3-[4-(2-neopentylamino-ethoxy)-benzoyl]-benzofuran hydrochloride
Yield: 45%
M.P.: 152°–154° C. (water)
2-n-Butyl-3-[4-(3-tert-butylamino-propoxy)-benzoyl]-benzofuran hydrochloride
Yield: 33%
M.P.: 142°–144° C. (isopropanol)
2-n-Butyl-3-[4-(3-neopentylamino-propoxy)-benzoyl]-benzofuran hydrochloride
Yield: 39%
M.P.: 140°–142° C. (water)

EXAMPLE 2

Preparation of 2-ethyl-3-[4-(2-tert-butylamino-ethoxy)-benzoyl]-benzofuran hydrochloride (a)

2-Ethyl-3-[4-(2-hydroxy-ethoxy)-benzoyl]-benzofuran

A suspension of 51.7 g (0.379 mole) of finely ground anhydrous potassium carbonate was stirred for 30 minutes at room-temperature in a solution of 49.9 g (0.18745 mole) of 2-ethyl-3-(4-hydroxy-benzoyl)-benzofuran in 400 ml of dimethyl formamide and then heated at about 50° C. for 20 minutes. After cooling, 118 g (0.937 mole) of 2-bromo-ethanol were added in one operation. Stirring was continued at a temperature of 60°–70° C. for 24 hours, after which the product was allowed to cool and poured into cold water. It was then extracted with ether, washed with water, then with a 10% aqueous solution of sodium hydroxide and again with water.

The product was dried over sodium sulphate, after which it was evaporated to dryness under vacuum. The oily residue was taken up in petroleum ether (40°–60° C.), stirred and filtered.

In this way, 56.7 g of 2-ethyl-3-[4-(2-hydroxy-ethoxy)-benzoyl]-benzofuran were obtained.
Yield: 97.4%.
M.P.: 78°–83° C.

By repeating the same procedure as described above and starting with the appropriate reactants, 2-n-butyl-3-[3-chloro-4-(2-hydroxy-ethoxy)-benzoyl]-benzofuran (an oily product) was prepared.
Yield: 97%

(b)

2-Ethyl-3-[4-(2-p-toluenesulphonyloxy-ethoxy)-benzoyl]-benzofuran

Under continuous stirring at a temperature of less than 20° C., 14 g (0.0734 mole) of p-toluene sulphonyl chloride were added in small amounts to 20 g (0.0644 mole) of 2-ethyl-3-[4-(2-hydroxy-ethoxy)-benzoyl]-benzofuran in 21 ml of pyridine. Stirring was continued for 4 h at room-temperature and the reactants were then poured into 120 ml of iced water containing 35 ml of concentrated hydrochloric acid. After that the product was extracted with benzene, carefully washed with water, dried over sodium sulphate and evaporated to dryness under vacuum. The still hot residue was taken up in petroleum ether (40°–60° C.), stirred and centrifuged.

In this way, 26 g of 2-ethyl-3-[4-(2-p-toluenesulphonyloxy-ethoxy)-benzoyl]-benzofuran were obtained.
Yield: 86.9%
M.P.: 95°–98° C.

Using the same procedure as that described above and starting with the appropriate reactants, 2-n-butyl-3-[3-chloro-4-(2-p-toluenesulphonyloxy-ethoxy)-benzoyl]-benzofuran (an oily product) was prepared.
Yield: 100%

(c)

2-Ethyl-3-[4-(2-tert-butylamino-ethoxy)-benzoyl]-benzofuran hydrochloride

A solution of 13 g (0.028 mole) of 2-ethyl-3-[4-(2-p-toluenesulphonyloxyethoxy)-benzoyl]-benzofuran and 22 g (0.29 mole) of tert-butylamino in 100 ml of benzene was heated at 50°–70° C. for 20 h in a closed vessel, the course of the reaction being monitored continuously by TLC. The product was evaporated to dryness and the residue taken up in diethyl ether and the ethereal solution was then washed with water to which a few ml of a 10% aqueous solution of sodium hydroxide had been added and again with water. Drying was carried out over sodium sulphate, the hydrochloride was formed and recrystallized in isopropanol.

In this way, 6.6 g of 2-ethyl-3-[4-(2-tert-butylamino-ethoxy)-benzoyl]-benzofuran hydrochloride were obtained.
Yield: 59%
M.P.: 173°–175° C.

In the same way and starting with the appropriate reactants, 2-ethyl-3-[4-(2-neopentylamino-ethoxy)-benzoyl]-benzofuran hydrochloride was prepared.
Yield: 42%
M.P.: 138°–139° C.

EXAMPLE 3

Preparation of 2-n-propyl-3-[4-(3-tert-butylamino-propoxy)-benzoyl]-benzofuran base and its hydrochloride (a) Free base A mixture of 14.2 g (0.0354 mole) of 2-n-propyl-3-[4-(3-bromo-propoxy)-benzoyl]-benzofuran dissolved in 100 ml of benzene and 26 g (0.0355 mole) of tert-butylamine dissolved in 60 ml of benzene was heated at 50°–80° C. for 20 to 24 hours, the course of the reaction being monitored continuously by TLC. Evaporation to dryness was carried out under vacuum and the residue was taken up in diethyl ether and water to which a few ml of 10% aqueous sodium hydroxide solution had been added. The product was extracted with ether and the extracts suitably washed with water, dried over anhydrous sodium sulphate and evaporated to dryness under vacuum.

In this way, 2-n-propyl-3-[4-(3-tert-butylaminopropoxy)-benzoyl]-benzofuran in the form of a free base (an oily product) was obtained.

N.M.R. spectrum (CDCl$_3$, reference:tetramethylsilane).

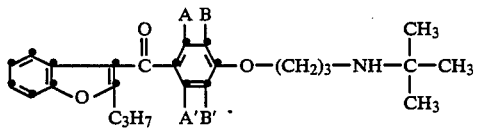

Chemical displacements
$\delta_H$AA': 7.73 ppm
$\delta_H$aromatic: 7.13 ppm (multiplet)
$\delta_H$BB': 6.84 ppm
$\delta_H$OCH$_2$: 4.07 ppm (triplet)

$$\delta_H \left( \begin{array}{c} \text{aromatic CH}_2 \\ \text{NCH}_2 \end{array} \right) : 2.83 \text{ ppm (multiplet)}$$

$$\delta_H \left( \begin{array}{c} \text{OCH}_2\text{—CH}_2 \\ \underline{\text{CH}_2}, \text{CH}_3 \end{array} \right) : 1.85 \text{ ppm (multiplet)}$$

$\delta_H \text{NH(CH}_3)_3$: 1.08 ppm
$\delta_H \text{CH}_2\text{—CH}_3$: 0.91 ppm (triplet)
Coupling constant
$J_{A,B} = 8.5$ cps (b) Hydrochloride The base obtained above was taken up in anhydrous diethyl ether acidified with an ethereal solution of hydrogen chloride and recrystallized in ethyl acetate. In this way, 5.6 g of 2-n-propyl-3-[4-(3-tert-butylaminopropoxy)-benzoyl]-benzofuran hydrochloride were obtained.
Yield: 37%
M.P.: 133°-135° C.

EXAMPLE 4

In accordance with known pharmaceutical techniques, a hard-gelatin capsule was prepared, containing the following ingredients:

| Ingredient | mg |
|---|---|
| Compound of the invention | 100.0 |
| Starches | 99.5 |
| Colloidal silica | 0.5 |
| | 200.0 |

I claim:

1. A benzofuran derivative corresponding to the formula:

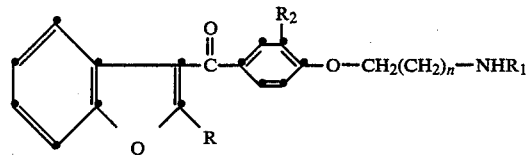

and the pharmaceutically acceptable acid addition salts thereof, wherein:
R represents an ethyl, n-propyl, isopropyl or n-butyl radical;
$R_1$ represents a branched-chain alkyl radical having from 4 to 7 carbon atoms wherein at least one of the carbon atoms does not bear a hydrogen atom;
$R_2$ represents hydrogen, chlorine or bromine;
n is 1 or 2.

2. A benzofuran derivative as claimed in claim 1 wherein $R_1$ represents a tert-butyl or neopentyl radical.

3. 2-n-Butyl-3-[4-(2-neopentylamino-ethoxy)-benzoyl]-benzofuran and the pharmaceutically acceptable acid addition salts thereof.

4. 2-Isopropyl-3-[3-chloro-4-(3-tert-butylaminopropoxy)-benzoyl]-benzofuran and the pharmaceutically acceptable acid addition salts thereof.

5. 2-Isopropyl-3-[3-chloro-4-(3-neopentylaminopropoxy)-benzoyl]-benzofuran and the pharmaceutically acceptable acid addition salts thereof.

6. 2-Isopropyl-3-[4-(3-neopentylamino-propoxy)-benzoyl]-benzofuran and the pharmaceutically acceptable acid addition salts thereof.

7. 2-n-Propyl-3-[4-(3-neopentylamino-propoxy)-benzoyl]-benzofuran and the pharmaceutically acceptable acid addition salts thereof.

8. A benzofuran derivative as claimed claim 1 wherein the pharmaceutically acceptable acid addition salt is the hydrochloride.

9. A benzofuran derivative as claimed in claim 2 wherein the pharmaceutically acceptable acid addition salt is the hydrochloride.

10. A benzofuran derivative as claimed in claim 3 wherein the pharmaceutically acceptable acid addition salt is the hydrochloride.

11. A benzofuran derivative as claimed in claim 4 wherein the pharmaceutically acceptable acid addition salt is the hydrochloride.

12. A benzofuran derivative as claimed in claim 5 wherein the pharmaceutically acceptable acid addition salt is the hydrochloride.

13. A benzofuran derivative as claimed in claim 6 wherein the pharmaceutically acceptable acid addition salt is the hydrochloride.

14. A benzofuran derivative as claimed in claim 7 wherein the pharmaceutically acceptable acid addition salt is the hydrochloride.

15. A pharmaceutical or veterinary composition for inducing calcium-antagonistic and antiadrenergic effects containing as essential active ingredient from 50 to 500 mg of at least one benzofuran derivative as claimed in claim 1 in association with a pharmaceutical carrier or excipient therefor.

16. A pharmaceutical or veterinary composition for inducing calcium-antagonistic and antiadrenergic effects containing as essential active ingredient from 50 to 500 mg of at least one benzofuran derivative as claimed in claim 2 in association with a pharmaceutical carrier or excipient therefor.

17. A pharmaceutical or veterinary composition for inducing calcium-antagonistic and antiadrenergic effects containing as essential active ingredient from 50 to 500 mg of at least one benzofuran derivative as claimed in claim 3 in association with a pharmaceutical carrier or excipient therefor.

18. A pharmaceutical or veterinary composition for inducing calcium-antagonistic and antiadrenergic effects containing as essential active ingredient for 50 to 500 mg of at least one benzofuran derivative as claimed in claim 4 in association with a pharmaceutical carrier or excipient therefor.

19. A pharmaceutical or veterinary composition for inducing calcium-antagonistic and antiadrenergic effects containing as essential active ingredient for 50 to 500 mg of at least one benzofuran derivative as claimed in claim 5 in association with a pharmaceutical carrier or excipient therefor.

20. A pharmaceutical or veterinary composition for inducing calcium-antagonistic and antiadrenergic effects containing as essential active ingredient for 50 to 500 mg of at least one benzofuran derivative as claimed in claim 6 in association with a pharmaceutical carrier or excipient therefor.

21. A pharmaceutical or veterinary composition for inducing calcium-antagonistic and antiadrenergic effects containing as essential active ingredient for 50 to 500 mg of at least one benzofuran derivative as claimed in claim 7 in association with a pharmaceutical carrier or excipient therefor.

22. A method of inducing calcium-antagonistic and antiadrenergic effects in a subject in need of such treatment which method comprises the administration to said subject of an effective dose of at least one benzofuran derivative as claimed in claim 1.

23. A method according to claim 22 wherein the effective dose is from 2 to 500 mg daily for a human being weighing 60 kgs.

* * * * *